US00PP21824P3

(12) United States Plant Patent
Bourne

(10) Patent No.: US PP21,824 P3
(45) Date of Patent: Mar. 29, 2011

(54) ***DIANTHUS* PLANT NAMED 'WP09 MAR05'**

(50) Latin Name: *Dianthus×hybrida*
Varietal Denomination: WP09 MAR05

(76) Inventor: Carolyn Grace Bourne, Dawlish (GB)

( * ) Notice: Subject to any disclaimer, the term of this patent is extended or adjusted under 35 U.S.C. 154(b) by 0 days.

(21) Appl. No.: 12/660,907

(22) Filed: Mar. 4, 2010

(65) Prior Publication Data

US 2010/0229270 P1 Sep. 9, 2010

(51) Int. Cl.
*A01H 5/00* (2006.01)

(52) U.S. Cl. ..... Plt./283

(58) Field of Classification Search ..... Plt./283
See application file for complete search history.

*Primary Examiner*—Annette H Para

(57) ABSTRACT

A new cultivar of *Dianthus* plant named 'WP09 MAR05' which is characterized by compact plant habit and early blooming fully double crimson colored flowers. In combination, these characteristics set 'WP09 MAR05' apart from all other existing varieties of *Dianthus* known to the inventor.

2 Drawing Sheets

Genus: *Dianthus.*
Species: ×*hybrida.*
Denomination: 'WP09 MAR05'.

BACKGROUND OF THE INVENTION

This application claims the benefit of priority under 35 U.S.C. 119(f) of the application for a grant of European Community Plant Breeders Rights which was filed for the instant plant variety on Mar. 9, 2009, Application Number 2009/0421.

The present invention relates to a new and distinct cultivar of hardy garden pink or carnation that is grown for use as a flowering plant for pots and containers and for planting in the garden and landscape. The new cultivar is known botanically as *Dianthus×hybrida* and will be referred to hereinafter by the cultivar name 'WP09 MAR05'.

'WP09 MAR05' is a complex hybrid plant that is the product of a breeding program started by the inventor in 1985. The breeding program is conducted in a cultivated area of Houndspool, Dawlish, Devon, United Kingdom. The inventor selected 'WP09 MAR05' in 2005 for its early season flowering and for its fully double crimson flowers which are fragrant and produced in profusion.

'WP09 MAR05' resulted from the controlled pollination between two unreleased and unpatented selections of *Dianthus* from the inventor's breeding program, namely Selection "98.02" as male parent and Selection "ASH22" as female parent.

'WP09 MAR05' is distinguishable from the male parent as follows: The height of the male parent is approximately two times the height of 'WP09 MAR05'. The length of the flower stems of the male parent is approximately two times the length of the flower stems of 'WP09 MAR05'. The flowers of the male parent are pink-magenta in color whereas the flowers of 'WP09 MAR05' are crimson in color.

'WP09 MAR05' is distinguishable from the female parent as follows: The flowers of the female parent are semi-double in form and are carmine in color, whereas the flowers of 'WP09 MAR05' are fully double and are crimson in color.

The variety of *Dianthus* which is considered by the inventor to most closely resemble 'WP09 MAR05' is *Dianthus* 'WP PASSION' (U.S. Plant patent Pending, application Ser. No. 12/220,573, filed Jul. 24, 2008.) 'WP09 MAR05' is distinguishable from this variety by plant height. Whereas plants of 'WP PASSION' are approximately 30 cm-35 cm in height after 9 months of growth, plants of 'WP09 MAR05' are 10 cm-13 cm in height after nine months of growth.

Asexual reproduction of 'WP09 MAR05' was first accomplished by the inventor in 2005 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP09 MAR05'. These traits in combination distinguish this cultivar from all other commercial varieties known to the inventor. 'WP09 MAR05' has not been tested under all possible conditions and phenotypic differences may be observed with variations in environmental, climatic and cultural conditions, however, without any variance in genotype.

1. *Dianthus* 'WP09 MAR05' exhibits a compact habit.
2. The flowers of *Dianthus* 'WP09 MAR05' are fully double.
3. The flowers of *Dianthus* 'WP09 MAR05' are crimson in color.
4. *Dianthus* 'WP09 MAR05' blooms from February through October.
5. *Dianthus* 'WP09 MAR05' exhibits grey-green foliage.
6. At nine months of age, the height of the foliage mound of *Dianthus* 'WP09 MAR05' is 10 cm to 13 cm, and the width is 12 cm to 15 cm.
7. *Dianthus* 'WP09 MAR05' is perennial and is hardy to −15° C.
8. *Dianthus* 'WP09 MAR05' is suitable for use as a flowering plant in pots and containers.

BRIEF DESCRIPTION OF THE DRAWINGS

The accompanying color drawings illustrate the overall appearance of the new *Dianthus* variety 'WP09 MAR05' showing colors as true as it is reasonably possible to obtain in colored reproductions of this type. Colors in the drawings may differ from the color values cited in the detailed botanical description, which accurately describe the actual colors of the new variety 'WP09 MAR05'.

The drawing labeled as FIG. 1 depicts an entire flowering plant.

Figure 1:
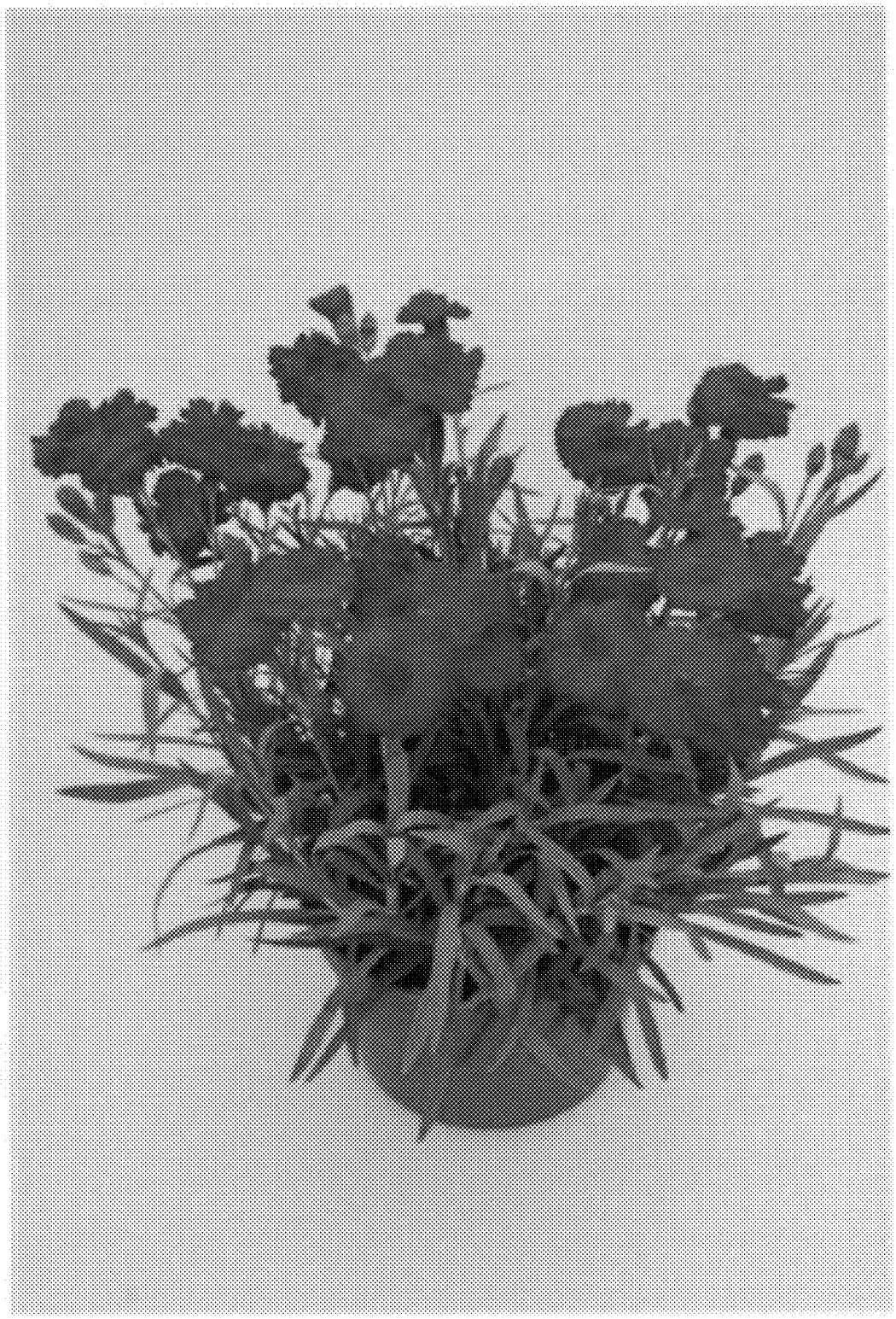
Figure 2:
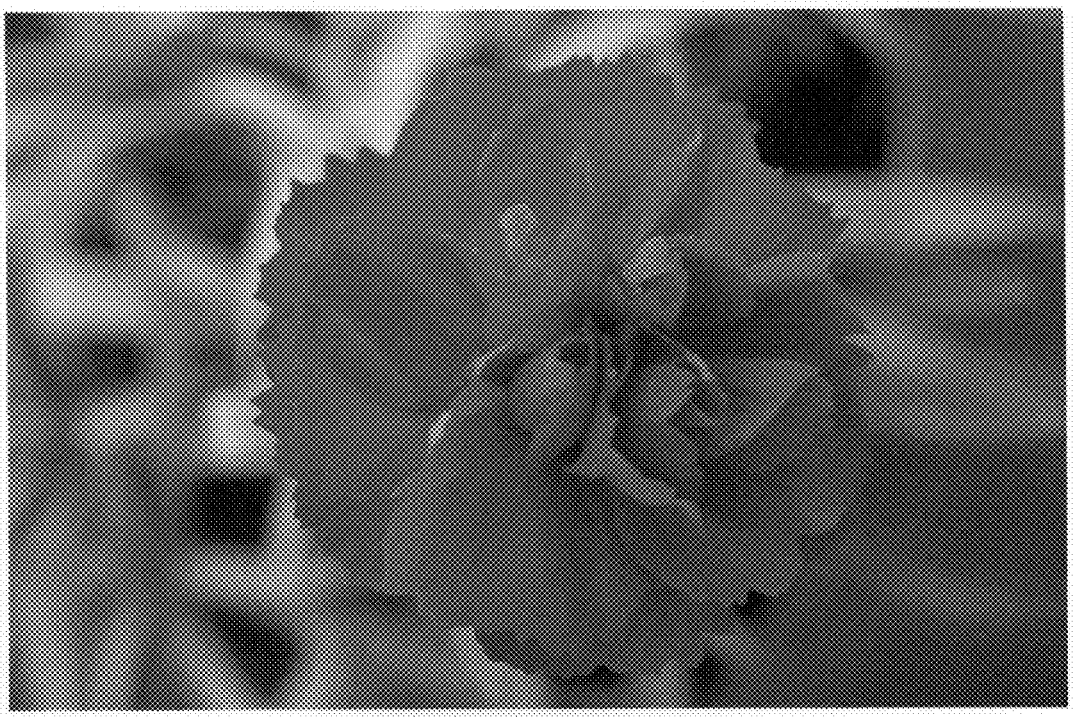

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP09 MAR05'. Data was collected in spring from 1.5-liter container plants in spring, and grown indoors in Devon, United Kingdom. The color determinations are in accordance with the 2002 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:

Family: Caryophyllaceae.

Genus: *Dianthus*.

Species: ×*hybrida*.

Denomination: 'WP09 MAR05'.

Parentage: A complex *Dianthus* hybrid whose immediate parents are unreleased hybrids from the inventor's breeding program, identified as follows:

Male parent: Unpatented selection of *Dianthus* from the inventor's breeding program, known as Selection "98.02".

Female parent: Unpatented selection of *Dianthus* from the inventor's breeding program, known as Selection "ASH22".

Plant type: Flowering perennial.

Use of plant: As a flowering plant in containers, window boxes, planters, pots and the garden.

Bloom period: February-October in Devon, UK.

Plant habit: A compact mound with many branches and stems upright.

Height of plant: 10 cm to 13 cm after 9 months.

Width of plant: 12 cm to 15 cm after 9 months.

Hardiness: Has survived in temperatures of minus 15 Centigrade, equivalent to USDA Hardiness Zone 7.

Root system: Many fibrous roots.

Propagation method: Vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: Mist propagation unit is required for satisfactory rooting of cuttings.

Crop time: 3 months starting in the Spring and 6 months starting in the Fall.

Plant stem:

*Shape.*—Cylindrical.

*Height.*—6 cm to 10 cm.

*Diameter.*—3 mm to 4 mm.

*Surface.*—Glabrous and glaucous.

*Color.*—145C.

*Branching.*—Numerous shoots from the axils of the lower leaves.

*Internode length* (*between nodes*).—6 mm to 10 mm.

Leaf:

*Type.*—Evergreen.

*Shape.*—Linear, straight.

*Division.*—Simple.

*Apex.*—Acute.

*Base.*—Decurrent.

*Venation.*—Not prominent.

*Margins.*—Entire.

*Arrangement.*—Opposite and spiraling on stem.

*Attachment.*—Sheathing.

*Surface adaxial.*—Glaucous.

*Surface abaxial.*—Glaucous.

*Fragrance.*—Absent.

*Dimensions.*—Length: 55 mm to 75 mm. Width: 4 mm to 5 mm.

*Color.*—Adaxial surface: 189A. Abaxial surface: 191A.

Inflorescence:

*Flower stem.*—Length: 90 mm to 120 mm. Width: 3 mm. Stem strength: Erect. Stem color: 189B.

*Inflorescence.*—Cymose.

*Type.*—Salviform, symmetrical.

*Development.*—Singly, in sequence from the uppermost bud.

Buds:

*Shape.*—Conical.

*Dimensions.*—11 mm in length and 10 mm in diameter.

*Color.*—138A except apex, 137A.

*Surface texture.*—Glabrous.

Flowers:

*Number.*—3 to 5 per stem.

*Pedicel dimensions.*—180 mm to 200 mm in length and 2 mm to 3 mm in width.

*Pedicel strength.*—Erect.

*Pedicel color.*—N189B.

*Flower dimensions.*—Length (including calyx): 35 mm. Diameter: 42 mm.

*Flower shape.*—Circular.

*Flower profile.*—Convex for the upper part of the corolla and concave for the lower part of the corolla.

*Lastingness.*—8 days at 20° C., on the plant.

*Fragrance.*—Medium perfume.

*Flowering period.*—February to October, in Devon, UK.

Corolla:

*Shape* (*upper part of corolla*).—Convex.

*Shape* (*lower part of corolla*).—Concave.

*Petal arrangement.*—Persistent, apopetalous, overlapping.

*Petal margin.*—Dentate.

*Indentation.*—1 mm to 2 mm deep.

*Petal texture.*—Soft.

*Flower type.*—Double.

*Petal number.*—20 to 25 true petals.

*Petal dimension.*—Length: 30 mm to 35 mm. Width: 20 mm.
*Color pattern.*—Self.
*Color of upper surface.*—Ground color of blade: Very iridescent, combination of 46a and 53A. Color of band across blade: No band. Color of middle of strap: 145C. Color of base of strap: 145D.
*Color of lower surface.*—Ground color of blade: Combination of 185A and 53A. Color of band across blade: No band. Color of middle of strap: 145C. Color of base of strap: 145D.
*Petal shape.*—Obdeltoid.
*Petal apex.*—Rounded, slightly flattened.
*Petal base.*—Tapers to narrow base, width at base 2 mm.
*Petal surface.*—Glabrous.

Calyx:
*Shape.*—Cylindrical.
*Sepal apex.*—Acuminate.
*Sepal base.*—Cuneate.
*Longitudinal profile.*—Flat.
*Dimensions.*—Length: 21 mm. Diameter: 9 mm.
*Sepals.*—Fused.
*Sepals number.*—5.
*Sepals color.*—189A-189B.
*Anthocyanin.*—Present.
*Splitting.*—Not observed.

Epicalyx:
*Bracts number.*—1 pair of two.
*Shape of outer lobe.*—Acuminate.
*Dimensions.*—Width: 6 mm. Length: 6 mm.
*Color.*—Upper surface 133B; lower surface 145B.
*Anthocyanin.*—Present.

Bracteoles:
*Number.*—1 pair of two.
*Dimensions.*—Width: 7 mm. Length: 8 mm.
*Color.*—Upper surface 133B; lower surface 145B.
*Anthocyanin.*—Present.

Reproductive organs:
*Stamens.*—Number: 0 to 10 filaments. Color of filaments: White. Dimensions: Length: 10 mm to 15 mm. Diameter: 0.5 mm.
*Anthers.*—Petaloid only: no true anthers have been observed.
*Pollen.*—Present occasionally.
*Pollen color.*—157A.
*Style.*—Number: 2. Shoulder: Absent. Color: White. Length: 15 mm to 20 mm. Width: 1 mm.
*Stigma.*—Number: Single. Color: 59B. Dimensions: N/A.
*Ovary.*—Position: Superior. Dimensions: Length: 6 mm to 7 mm. Diameter: 3 mm to 4 mm. Shape: Spindle. Color (upper surface): 145B. Color (lower surface): 145C.
*Seed.*—Seed has not been observed.

It is claimed:

1. A new and distinct cultivar of *Dianthus* plant named 'WP09 MAR05' as described and illustrated herein.

* * * * *